(12) United States Patent
Hajishah et al.

(10) Patent No.: US 10,864,113 B2
(45) Date of Patent: Dec. 15, 2020

(54) SYSTEM AND APPARATUS FOR SWITCH AND FOOT PEDAL TAP DETECTION AND FILTERING

(71) Applicant: Johnson & Johnson Surgical Vision, Inc., Santa Ana, CA (US)

(72) Inventors: Abraham Hajishah, Irvine, CA (US); Mitchell W. Mallough, Irvine, CA (US); Joseph E. Pedroza, Vista, CA (US)

(73) Assignee: Johnson & Johnson Surgical Vision, Inc., Santa Ana, CA (US)

(*) Notice: Subject to any disclaimer, the term of this patent is extended or adjusted under 35 U.S.C. 154(b) by 204 days.

(21) Appl. No.: 16/045,533

(22) Filed: Jul. 25, 2018

(65) Prior Publication Data

US 2018/0325730 A1 Nov. 15, 2018

Related U.S. Application Data

(62) Division of application No. 14/693,077, filed on Apr. 22, 2015, now Pat. No. 10,058,450.

(60) Provisional application No. 61/983,324, filed on Apr. 23, 2014.

(51) Int. Cl.
*A61F 9/007* (2006.01)
*H01H 21/26* (2006.01)
*A61B 17/00* (2006.01)

(52) U.S. Cl.
CPC .......... *A61F 9/00745* (2013.01); *A61F 9/007* (2013.01); *H01H 21/26* (2013.01); *A61B 2017/00221* (2013.01); *A61B 2017/00973* (2013.01)

(58) Field of Classification Search
CPC .......... A61B 17/32; A61B 2017/00973; A61B 2017/00977; A61F 9/007–0136; A61F 2009/00842–00897
See application file for complete search history.

(56) References Cited

U.S. PATENT DOCUMENTS 4,970,656 A 11/1990 Lo et al.
6,266,387 B1 * 7/2001 Gscheidmeier ........ A61B 6/032
378/116

FOREIGN PATENT DOCUMENTS

JP 2006068396 A 3/2006

OTHER PUBLICATIONS

International Search Report and Written Opinion for Application No. PCT/US2015/027027, dated Jul. 6, 2015, 10 pages.

* cited by examiner

*Primary Examiner* — Robert A Lynch
(74) *Attorney, Agent, or Firm* — Johnson & Johnson Surgical Vision, Inc.

(57) ABSTRACT

An ocular surgical apparatus is provided, including a surgical control device such as a foot pedal configured to be employed to control at least one ocular surgical parameter, and a controller configured to receive a series of values from the surgical control device and evaluate the series of values provided from the surgical control device, the series of values provided using a buffer comprising a detection area and an exclusion area. Presence of a desired value in the detection area and an absence of a contrary indication in the exclusion area is determined by the controller to indicate a switch associated with the surgical control device is requested by a user of the surgical control device.

9 Claims, 10 Drawing Sheets

SYSTEM AND APPARATUS FOR SWITCH AND FOOT PEDAL TAP DETECTION AND FILTERING

CROSS REFERENCE TO RELATED APPLICATION

This application is a divisional of and claims priority to U.S. patent application Ser. No. 14/693,077, filed on Apr. 22, 2015, which claims priority to U.S. Provisional Application No. 61/983,324, filed on Apr. 23, 2014, entitled "System and Apparatus for Switch and Foot Pedal Tap Detection and Filtering," all of which are hereby incorporated by reference in their entirety for all purposes as if set forth herein.

BACKGROUND

Field of the Invention

The present invention relates generally to the field of surgical procedures, and more specifically to the enhanced control of medical devices such as foot pedals and switches used in surgical procedures.

Description of the Related Art

Ocular surgical procedures include phacoemulsification, diathermy, and vitrectomy procedures.

Phacoemulsification refers to a method of lens and cataract extraction from an eye. The procedure includes an ultrasonically vibrated needle which is inserted through a very small incision in the cornea in order to provide energy for emulsifying or breaking up of the lens and cataract which then can be aspirated and removed through the incision.

Diathermy refers to a method of cautery to seal severed or ruptured blood vessels. Diathermy is used in ophthalmic surgery to halt bleeding associated with surgical incisions.

Vitrectomy surgery has been successfully employed during cataract surgery when the posterior capsular bag has been broken and in the treatment of retinal detachments resulting from tears or holes in the retina. In cataract surgery, the same incision used for the phacoemulsification handpiece is used for inserting the vitrector to remove the vitreous gel. Vitrectomy surgery typically involves removal of vitreous gel and may utilize three small incisions in the pars plana of the patient's eye. These incisions allow the surgeon to pass three separate instruments into the patient's eye to affect the ocular procedure. The surgical instruments typically include a vitreous cutting device, an illumination source, and an infusion port.

Phacoemulsification and vitrectomy procedures may require fluid control, namely control over aspiration and irrigation to the ocular region, and employ a handpiece that is typically electrically driven and must be controlled. As the surgeon is employing the handpiece and possibly a fluid handpiece during surgery, control is provided to the surgeon via a foot pedal. Foot pedals vary in design, but more modern foot pedals include a treadle that can be moved in a fore-and-aft direction (a pitch motion) and in a left-and-right direction (a yaw motion). Hard switches are also provided, where the switches typically provide a toggle functionality and/or an on-off functionality. Control can be provided for various device components and operations for the phacoemulsification, diathermy or vitrectomy machine, including control of fluid flow, entry into various modes, electrical parameters, speed parameters (e.g. cut speed), and so forth.

One of the issues with traditional foot pedals is the dexterity required to perform multiple foot pedal operations, i.e. engage the foot pedal at multiple positions or to perform more than one function. For example, a surgeon may be controlling fluid flow using movement of the treadle in the pitch and yaw axes, attaining a certain position to achieve desired fluid flow balance, and may then need to engage a switch to raise or lower the height of an irrigation source, such as an irrigation bottle. It can be difficult to maintain the desired level of fluid flow, i.e. maintain the desired treadle position, and at the same time engage a footswitch without either disrupting fluid flow or altering fluid flow and subsequently attempting to reacquire the same fluid flow state in this example. Foot pedal switches have been offered at different positions on different foot pedals, but generally are located proximate the treadle, such as at the sides, near the base, or at the forward tip of the treadle. In certain foot pedal designs, top switches are provided that are on the underside of the top of an enclosed foot pedal.

Such foot pedal switches may be electromechanical, and such switches tend to increase the cost and complexity of foot pedal design, and have an increased chance of failure. As with any device having multiple components, failure of one component can result in the device being unusable in its entirety, and loss of a foot pedal or any of its functions can be highly problematic.

Further, existing foot pedal switches can be sensitive and at times inaccurate as far as detection of engagement. Certain transient or inadvertent physical actions may be considered switch engagements when in actuality they are nothing more than spurious events. Such sensitivities are undesirable and should be minimized.

Based on the foregoing, it would be advantageous to provide a foot pedal design that limits the need for foot pedal switch functionality, and/or provides an ability to distinguish engagement of a foot pedal switch from an inadvertent transient or momentary occurrence. Such a design would afford a surgeon the ability to engage desired phacoemulsification, diathermy, or vitrectomy functions with less need to employ foot pedal switches, and/or obtain better performance from foot pedal switches.

SUMMARY

Thus according to one aspect of the present invention, there is provided an ocular surgical apparatus comprising a surgical control device, such as a foot pedal, configured to be employed to control at least one ocular surgical parameter, and a controller configured to receive a series of values from the surgical control device and evaluate the series of values provided from the surgical control device, the series of values provided using a buffer comprising a detection area and an exclusion area. Presence of a desired value in the detection area and an absence of a contrary indication in the exclusion area is determined by the controller to indicate a switch associated with the surgical control device is requested by a user of the surgical control device.

According to another embodiment of the present design, there is provided a method for use in an ocular surgical device, comprising operating a surgical control device (e.g. foot pedal) to control at least one ocular surgical parameter, receiving a series of values from the surgical control device using a buffer comprising a detection area and an exclusion area, and controlling a parameter of the ocular surgical device based on contents of the buffer. Presence of a desired value in the detection area and an absence of a contrary indication in the exclusion area indicate a switch associated with the surgical control device is requested by a user of the surgical control device.

According to another embodiment of the present design, there is provided a surgical control device (e.g. foot pedal) configured to be employed to control at least one ocular surgical parameter and a controller configured to receive a series of values from the surgical control device, evaluate the series of values provided from the surgical control device, the series of values provided using a buffer comprising a detection area and an exclusion area, and control an attribute of the ocular surgical apparatus when the series of values indicates a user desires a switch of the attribute based on user input received from the surgical control device. Presence of a desired value in the detection area and an absence of a contrary indication in the exclusion area is determined by the controller to indicate a switch associated with the surgical control device is requested by the user of the surgical control device.

Other features and advantages of the present invention should be apparent from the following description of exemplary embodiments, which illustrate, by way of example, aspects of the invention.

DETAILED DESCRIPTION

The following description and the drawings illustrate specific embodiments sufficiently to enable those skilled in the art to practice the system and method described. Other embodiments may incorporate structural, logical, process and other changes. Examples merely typify possible variations. Individual components and functions are generally optional unless explicitly required, and the sequence of operations may vary. Portions and features of some embodiments may be included in or substituted for those of others.

The present design provides a system and method for foot pedal control that detects foot pedal treadle zone or switch readings as conforming to desired foot pedal switch engagement, using at least one running buffer including fields specific to each switch or foot pedal treadle zone, and deciding under certain conditions whether a click or tap of a switch has been detected.

The present design will be discussed herein with a particular emphasis on a medical or hospital environment where a surgeon or health care practitioner performs. For example, an embodiment of the present design is a phacoemulsification surgical system that comprises an integrated high-speed control module for the vitrectomy handpiece. The surgeon may adjust or set the cutting speed via a graphical user interface (GUI) module or a foot pedal to control the high-speed pneumatic vitrectomy handpiece.

Figure 1:
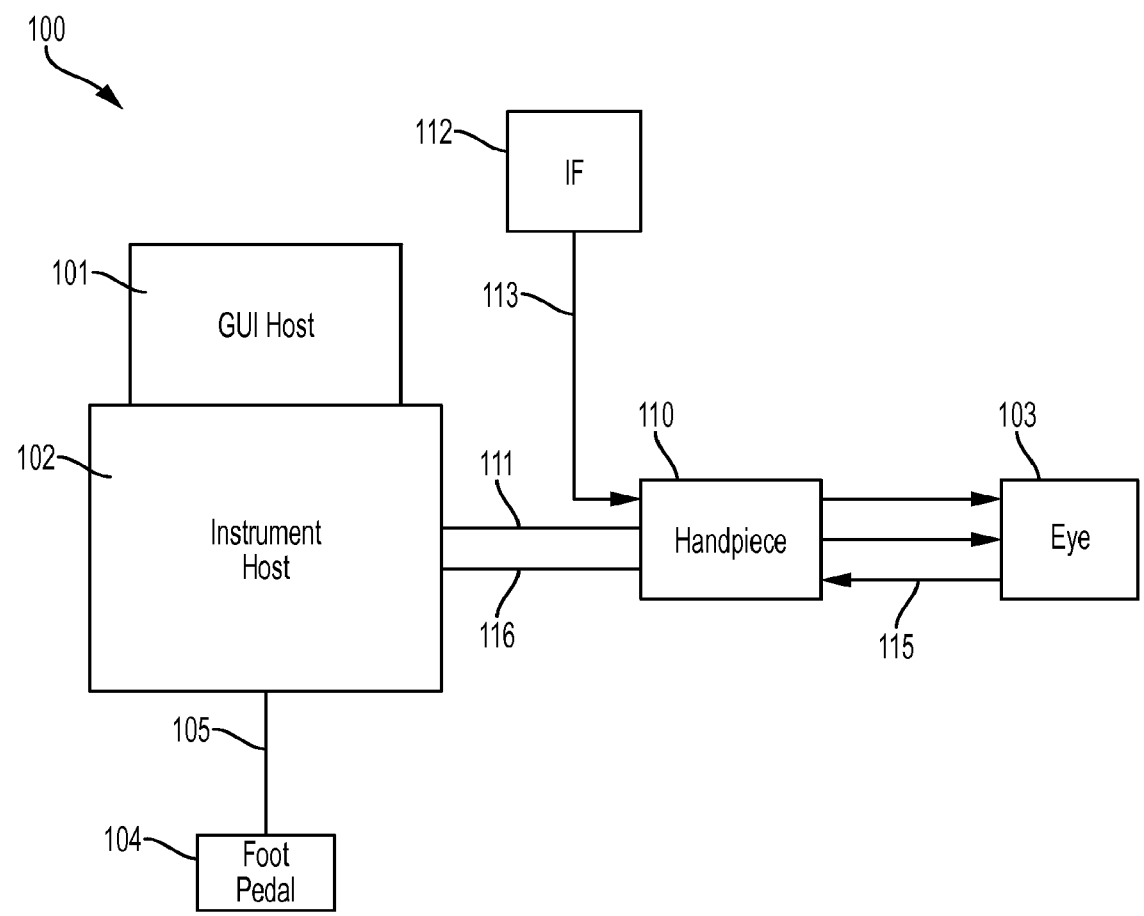
FIG. 1 is a block diagram illustrates an exemplary phacoemulsification/diathermy/vitrectomy system in accordance with the present design.

FIG. 1 illustrates an exemplary phacoemulsification/diathermy/vitrectomy system 100 in a functional block diagram to show the components and interfaces for a safety critical medical instrument system that may be employed in accordance with the present design. GUI host 101 and instrument host 102 reside on a single-board computer and communicate through inter-process communication. A processor (not shown) may be provided to control instrument host 102 and GUI host 101. Instrument host 102 typically takes the form of a computational device in the arrangement shown, but other arrangements are possible. An interface communications cable (not shown) may be connected to instrument host 102 for distribution of instrument sensor data, and may distribute instrument settings and parameter information to other systems, subsystems and modules within and external to the instrument host 102. An interface communications cable may be connected or realized on any other subsystem (not shown) that could accommodate such an interface device able to distribute required data.

Foot pedal 104 may also be provided as part of phacoemulsification/diathermy/vitrectomy system 100. A switch module associated with foot pedal 104 may transmit control signals relating foot pedal physical and virtual switch position information as input to the instrument host 102 over serial communications cable 105. A wireless foot pedal may alternately be provided. Instrument host 102 may include a database file system for storing configuration parameter values, programs, and other data saved in a storage device (not shown).

Also shown in FIG. 1 is a phacoemulsification handpiece 110 that includes a needle and electrical means, typically a piezoelectric crystal, for ultrasonically vibrating the needle. The instrument host 102 supplies power on line 111 to a phacoemulsification handpiece 110. An irrigation fluid source 112 can be fluidly coupled to handpiece 110 through line 113. The irrigation fluid and ultrasonic power are applied by handpiece 110 to an eye, or affected area or region, indicated diagrammatically by block 103. Alternatively, the irrigation source may be routed to eye 103 through a separate pathway independent of the handpiece. Aspiration is provided to eye 103 by a pump (not shown), such as a peristaltic pump and/or Venturi pump, via the instrument host 102, through lines 115 and 116. A surgeon/operator may select an amplitude of electrical pulses using the handpiece, or via the instrument host 102 and GUI host 101, or using foot pedal 104.

Figure 2A:
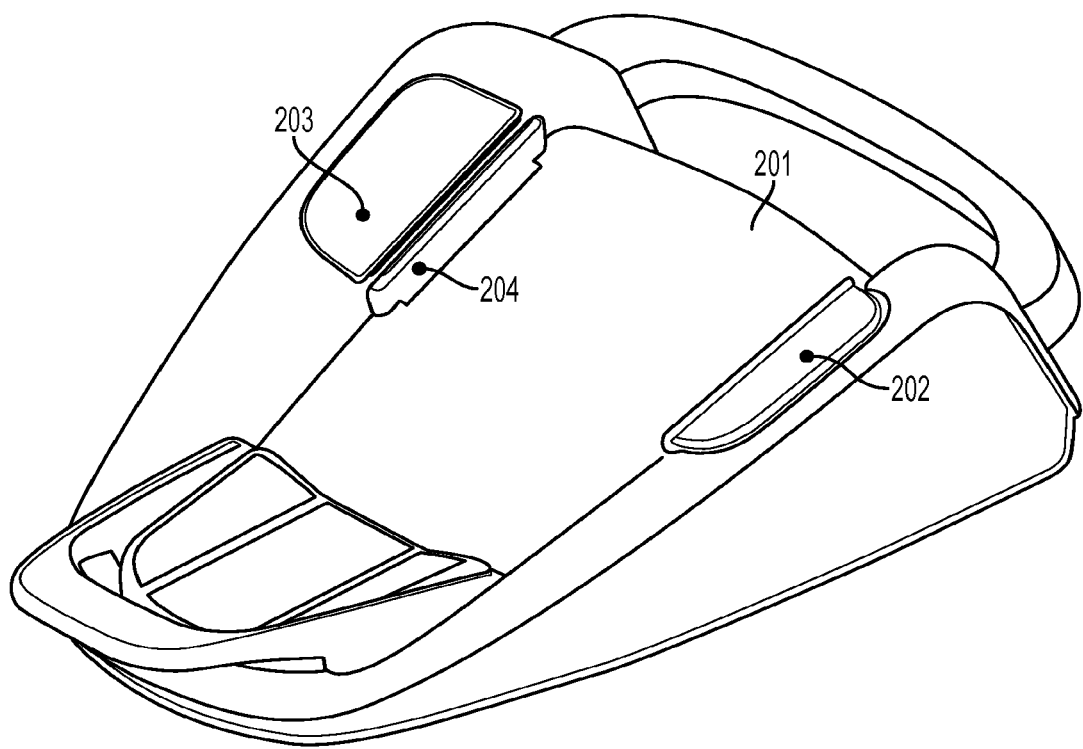
FIG. 2A illustrates an example of a foot pedal that may be employed with the current design.
Figure 2B:
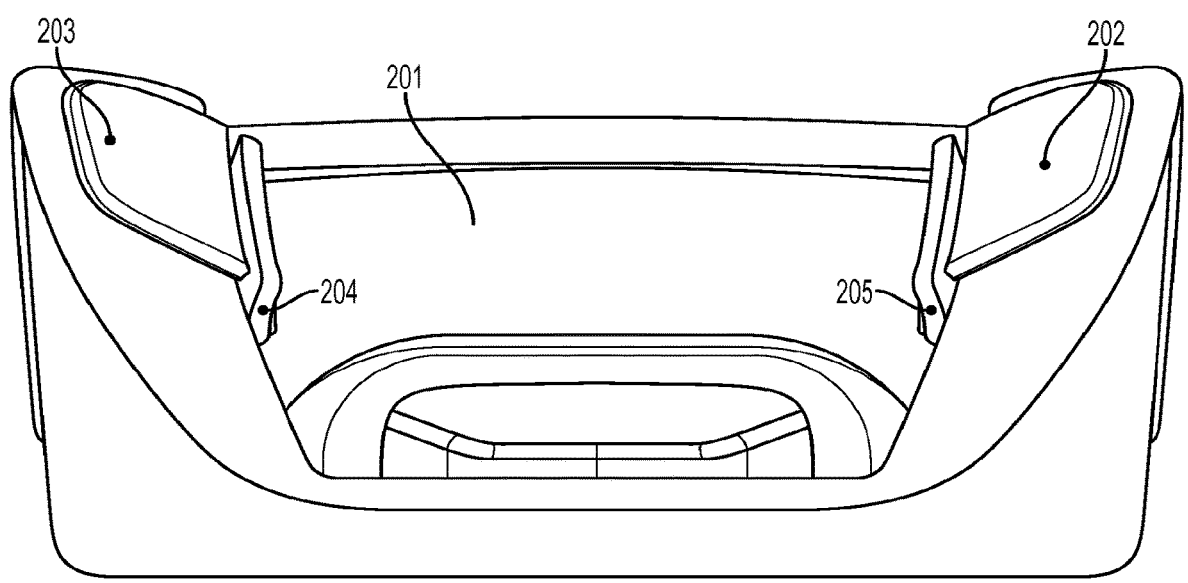
FIG. 2B is an alternate view of a foot pedal that may be employed with the current design.

One example of a foot pedal such as foot pedal 104 for use in such a system is presented in FIG. 2A. FIG. 2A shows treadle 201 and switches 202 and 203. A further switch 204 is shown in this view. FIG. 2B illustrates switches 202, 203, and 204, and further switch 205. The depiction in FIGS. 2A and 2B are one example of a foot pedal, but other foot pedals may be used with this design. Other foot pedals can have different switch and treadle configurations, such as heel, toe, and top switches.

As noted, one aspect of the present design seeks to minimize the need to employ the switches on the foot pedal by providing a unique control mechanism. The control mechanism takes treadle orientation and divides angular regions of travel of the treadle into zones. When a surgeon is in a zone and taps the treadle, depending upon the nature of the tap, i.e. time duration, the tap may be considered to have engaged a particular switch without the need to orient his foot elsewhere on the foot pedal or "stomp" or otherwise engage a particular hardware electromechanical switch with his foot.

Figure 3:
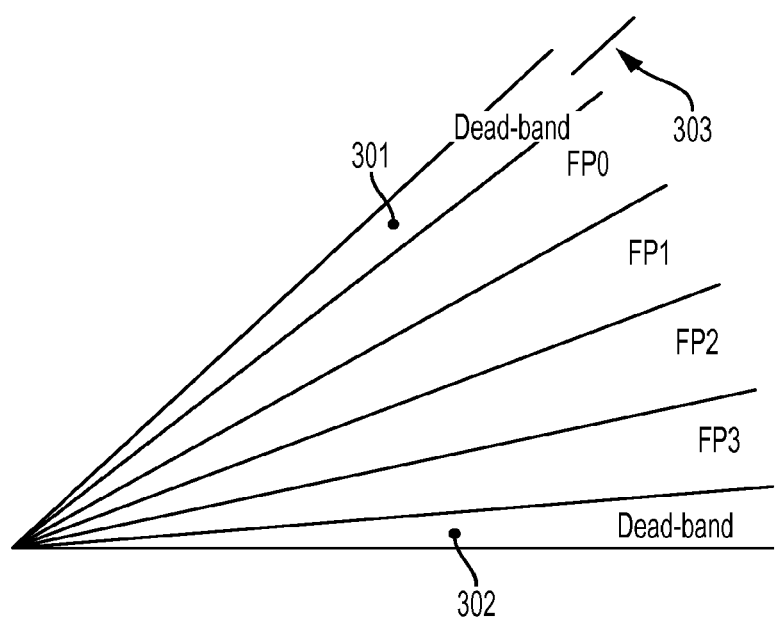
FIG. 3 illustrates a region of travel in the pitch direction for the treadle of a foot pedal.

FIG. 3 illustrates a region of travel in the pitch direction for the treadle of a foot pedal. At an unengaged state, the treadle will typically be in the dead band zone 301. Zones FP0, FP1, FP2, and FP3 are provided, as well as a further dead band zone 302. In operation, one movement to engage a switch may be for the surgeon to move the treadle into region FP1 and a return to FP0 to indicate a desired switch using pitch mode. This is an example, and other implementations are possible.

Zero switch 303 is a location within the dead band zone 301 that indicates that a user has fully released the treadle of the foot pedal. The zero switch 303 may be located anywhere within the dead band zone, and in one embodiment the zero switch 303 may be at, near, or past the center point of the dead band 301 and closer to the FP0 zone.

Figure 4:
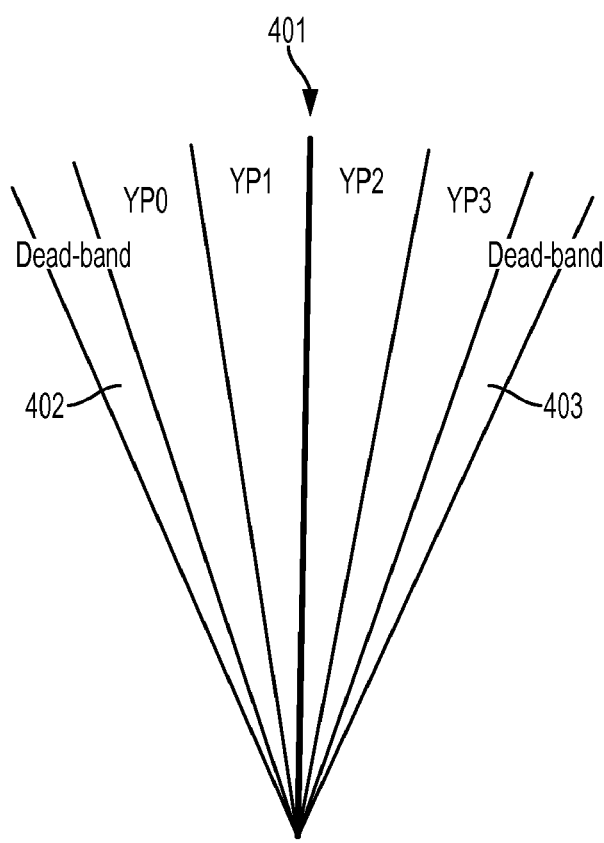
FIG. 4 shows the full range of travel in the yaw or side-to-side direction for the treadle of a foot pedal.

FIG. 4 shows the full range of travel in the yaw or side-to-side direction, Two outer dead band zones are provided, and zones labeled YP0, YP1, YP2, and YP3 are shown, where under normal conditions the treadle reverts to or near the center position 401. One way to indicate a switch is to turn the treadle into zone YP0 or YP3 and return to or near the center position 401. Such movement indicates a desired switch, i.e. in the yaw mode this movement is the "tap" that indicates a switch using yaw mode. Dead band zones 402 and 403 are shown in this view. Again, this is an example, and other operations are possible.

Figure 5:
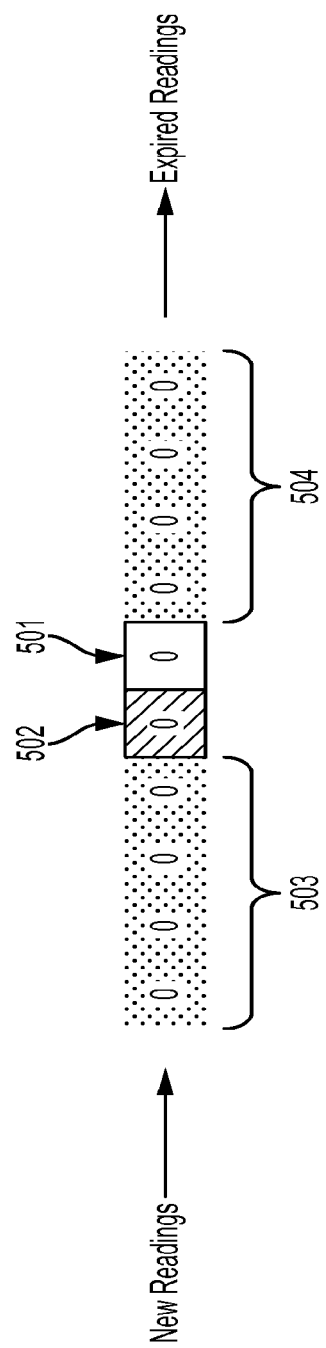
FIG. 5 illustrates the running first in, first out (FIFO) buffer elements in an example 10 element buffer.

The present design employs a running buffer that may be of any size, but for purposes of this particular example, ten buffer elements are presented. FIG. 5 illustrates the running buffer elements in a 10 element buffer, where new readings are added on the left side and the last or oldest reading is removed, and all buffer elements progress sequentially from left to right. As an example, all buffer elements may include zero, and when a switch is selected or a foot pedal treadle enters a zone, a value such as one is provided in the leftmost element in this view. In the next frame, which may be X milliseconds later, the 1 value moves to the second element from the left and progresses from left to right.

FIG. 5 shows a primary detection slot 501, indicating a primary slot evaluated to determine the status of the variable, be it a switch selection, change of mode, tap of a foot pedal treadle in a zone, entry of the treadle into a zone, or otherwise. Slot 502 is a secondary limitation, generally indicating that the value entered in this region could be anything—a zero, one, or other number, and depending upon whether the running buffer is detecting for a valid switch click, foot pedal tap, and so forth, determine whether the value entry has an effect on the status of the primary detection region 501. Finally, two areas 503 and 504 are shown, where these areas regions indicate tertiary exclusions, indicating any value other than zero provided in these areas, i.e. in any field in the area, is a contrary or exclusionary indication. Such a contrary or exclusionary indication means that even if the region or slot 501 includes a value of "1," a value of "1" in any of these regions negates the status of the switch, tap, mode, or function. For example, if region 501 includes a "1," indicating a switch selection, and area 503 includes a "1" in the second region from the left, the "1" in region 501 is negated by the "1" in area 503 such that no switch selection has occurred.

As may be appreciated, different regions may be primary detection areas, secondary limitation areas, and tertiary exclusion areas, and such areas may be contiguous or discontinuous. Further, logic may be employed to vary functionality, such as if a primary detection is indicated and a tertiary exclusion is also indicated, the secondary limitation acts as a "tie-breaker," such that a value of "1" in the secondary region indicates selection of the switch, tap, mode, or function associated with the primary detection area. Further region hierarchies may be provided.

Figure 6:
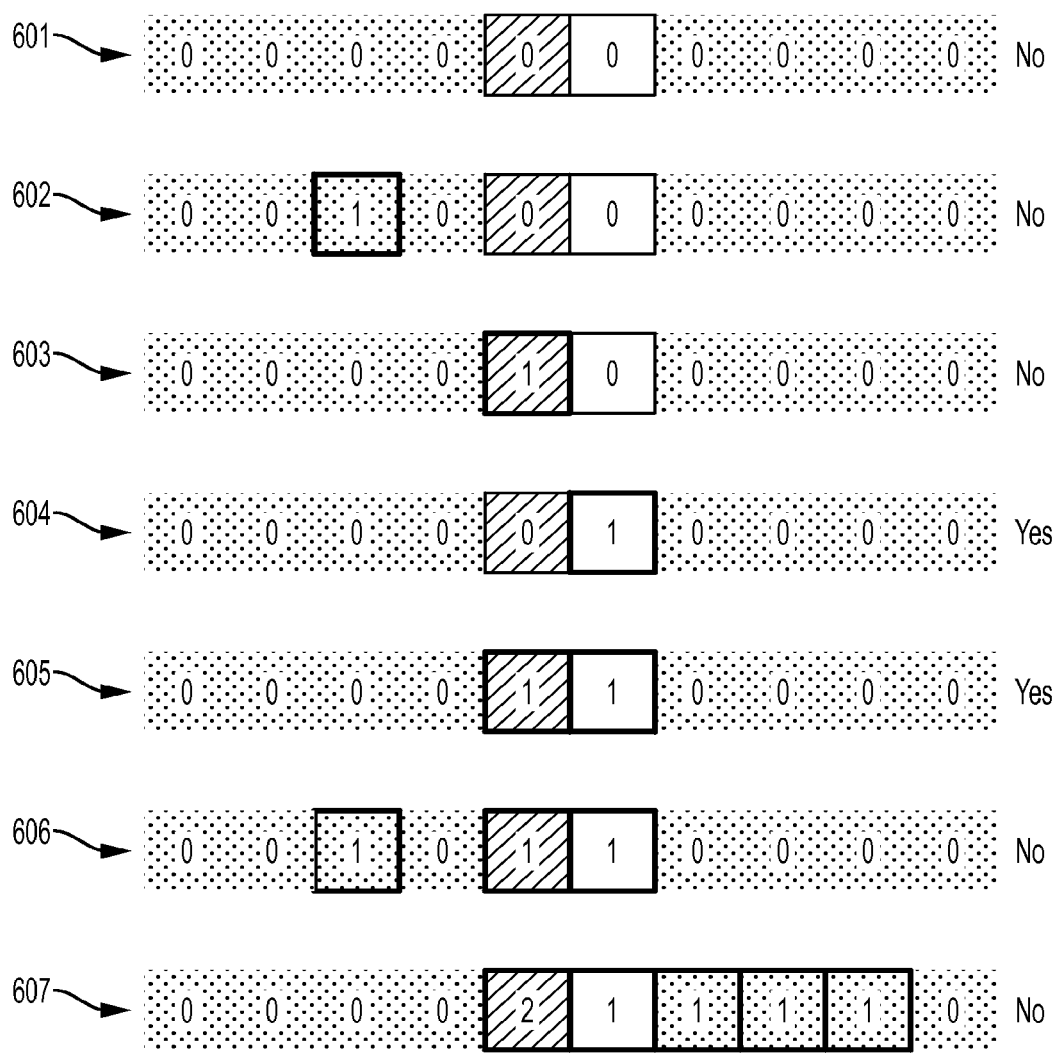
FIG. 6 is an example of switch click filtering, nonsequential in time and showing discrete "snapshots" in time.
Figure 7:
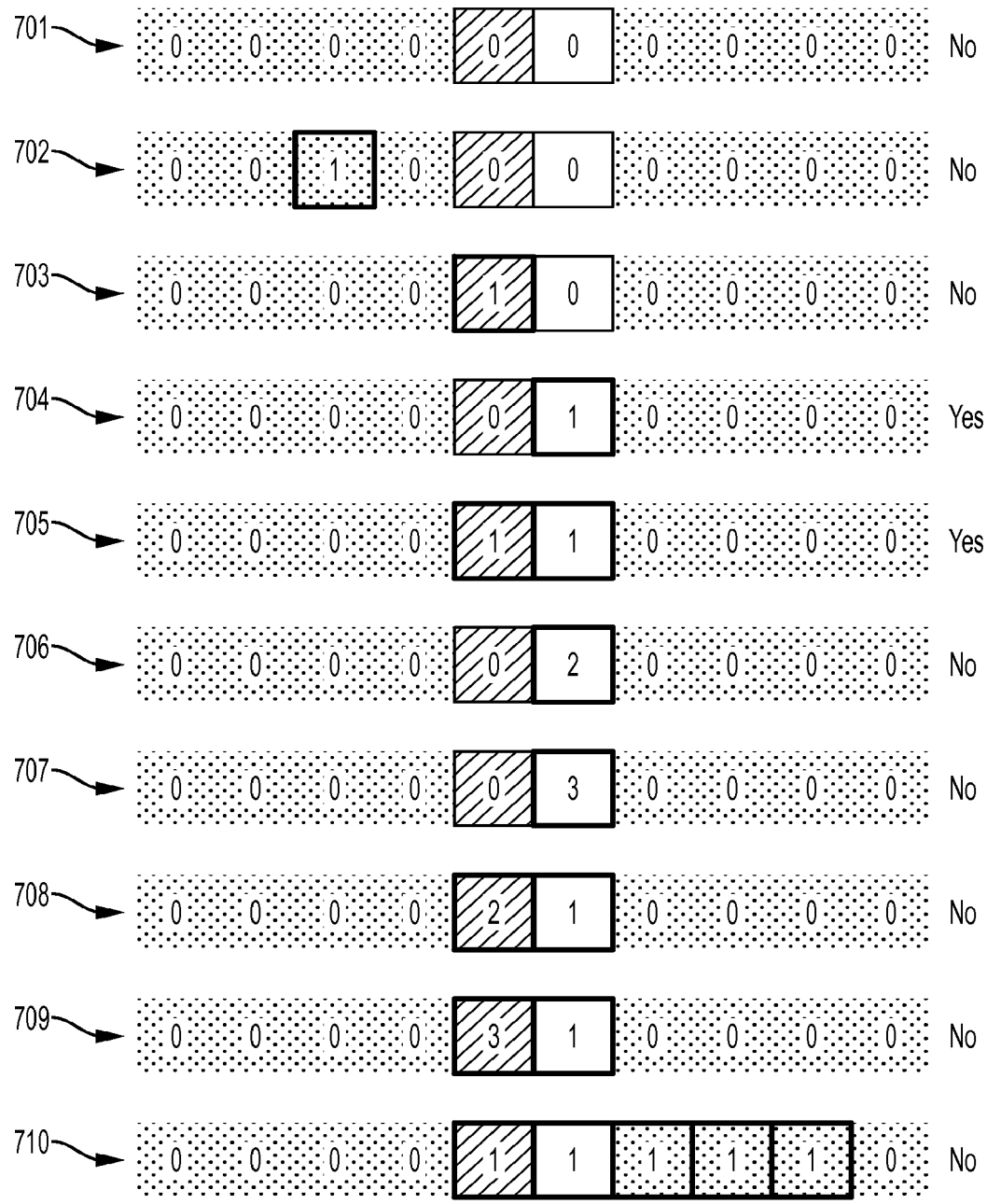
FIG. 7 illustrates an example of foot pedal tap filtering such as when the foot pedal treadle enters a desired zone in order to effectuate a switch function, again nonsequential in time and illustrating discrete "snapshots" in time.

FIG. 6 presents a switch click filtering embodiment, wherein the system seeks to determine whether a signal indicating a switch has been activated is a valid switch click, i.e. a switch was meant to be activated, based on multiple readings over a period of time. The running buffer examples in FIG. 6 and FIG. 7 represent discrete snapshots in time and from top to bottom are not meant to represent a sequential set of buffer states. These are "snapshots" in time representing individual and discrete states of a running buffer that indicate valid and invalid states for the validation of the receipt of a switch selection, e.g. a button click or tap. FIG. 6 follows the primary detection, secondary limitation, and tertiary exclusion requirements of FIG. 5 and operates as discussed with respect to FIG. 5, i.e. new readings come in from the left and the rightmost reading is dropped every frame, and primary detection is indicated in the fifth region from the left in this view.

From FIG. 6, buffer 601 is filled with zeros, indicating no switch selection has occurred—the value in the primary detection area is zero. In buffer 602, not only is there a "0" in the primary detection region, there is a contrary "1" in a tertiary exclusion region, and thus no valid click has occurred or been detected, and as a result the function associated with the switch is not effectuated. Buffer 603 shows a "1" in the secondary limitation area, but in this scenario, this region has no bearing on the switch selection and again no valid "click" has occurred. In buffer 604, a "1" is provided in the primary detection region, no contrary indications are presented, and thus the switch is considered selected as a valid "click" and the function associated with the switch is effectuated. Buffer 605 also has a "1" in the primary detection region and a "1" in the secondary detection region, and thus the switch status is "valid." Buffer 606 illustrates positive indications in both the primary detection region and the secondary limitation region, but a contrary indication in a tertiary exclusion region. Thus the positive value in the tertiary exclusion area overrides the positive indication in the primary detection area. As a result, no switch indication is provided. Finally, in region 607, "1" values are provided in the primary detection and secondary limitation area, but several contrary indications are provided, again resulting in a "no valid click" condition or state.

FIG. 7 similarly shows discrete and nonsequential buffer states and is meant for instructional purposes. In general, FIG. 7 represents foot pedal tap filtering, where the foot pedal is used to indicate sensing of a change in function. For example, referring to FIG. 3, moving into FP1 then returning to FP0 in the pitch direction may be considered a switch such that the tap of the foot pedal registers as activating a particular function of the system, and the buffer regions in FIG. 7 represent particular conditions, i.e. the treadle is in region FP0, in region FP1, in region FP2, in region FP3, in a dead zone, etc.

From FIG. 7, buffer 701 is filled with zeros and thus no valid tap is considered to have occurred. In buffer 702, not only is there a "0" in the primary detection region, there is a contrary "1" in a tertiary exclusion region, and thus no valid tap selection has occurred so the function associated with the switch/tap does not occur. Buffer 703 shows a "1" in the secondary limitation area, in this example this region has a bearing on the switch selection to determine what foot pedal position the treadle is in as the switch or recognized tap is only activated in FP1 so the secondary limitation will be exclusionary for everything except a "0" or a "1", where the number corresponds to the foot pedal position (e.g. FP0 equals "0"; FP1 equals 1; FP2 equals 2; FP3 equals 3, and so forth). Thus, for buffer 703 no valid tap selection has occurred.

In buffer 704, a "1" is provided in the primary detection region, no contrary indications are presented, and thus the tap is considered valid. Buffer 705 also has a "1" in the primary detection region and a "1" in the secondary detection region, and thus the switch status is "valid." Buffer 706 includes a value of "2" in the primary detection area, which is not an accepted tap condition of "1" and the result is that no valid tap has occurred with the arrangement of buffer 706. Similarly, buffer 707 provides a value of "3" in the primary detection area, and again, since "3" is not "1," the tap is not valid.

Buffer 708 illustrates another particular situation wherein the primary detection area includes a "1," but the secondary limitation includes a "2" rather than a "1" or zero. This may be an error condition, in that the only valid values for secondary limitation regions is to include a "1" or a zero, and the number "2" or any other number is invalid. Thus even though the primary detection area is "1" and the secondary limitation area is essential to the buffer and the fact that the value is outside the acceptable values is an error and is considered to be a non-switch or invalid tap condition. Similarly, buffer 709 includes the value "3" in the secondary limitation area and is thus invalid, and no valid tap has occurred. Finally, buffer 710 includes "1" values in the primary detection and secondary limitation areas, but several contrary indications are provided, again resulting in a "no valid tap" condition or state.

In general, the functionality described herein and the assessment of buffer, area, and region contents can be performed by a controller located with the foot pedal or with a remote device, such as a phacoemulsification/diathermy/vitrectomy device. In general, any type of device that can make the determinations required, such as evaluating the buffer contents presented in FIGS. 6 and 7, can be employed, and such functionality may be provided in hardware or software and/or distributed within one or more than one computing or processing devices.

Figure 8:
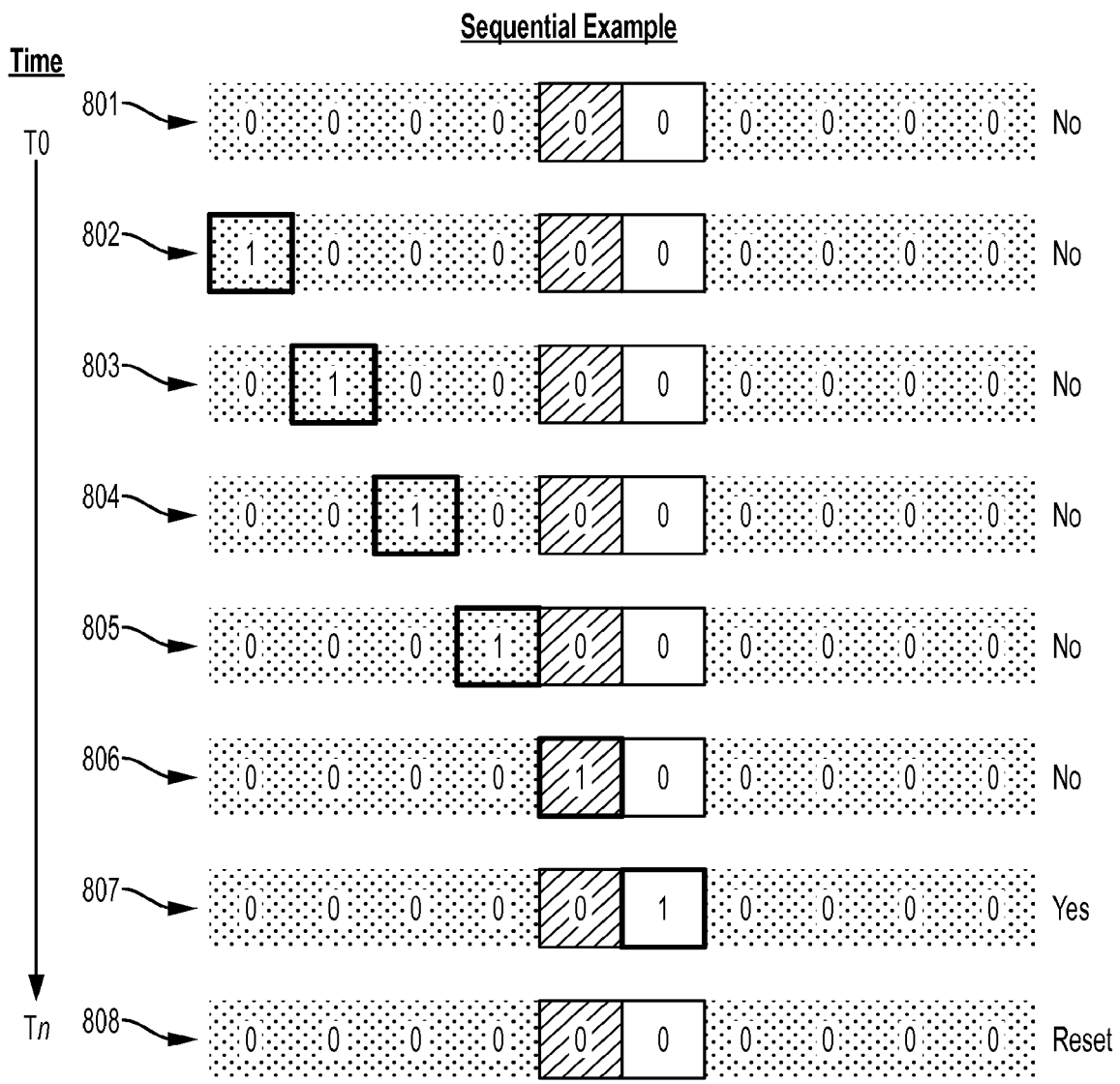
FIG. 8 is a sequential example of switch click filtering.

FIG. 8 illustrates a sequential example for a click or pitch based tap, but is applicable to switch clicks or other types of taps. The number "1" indicates an entry into region FP1, indicating a valid pitch tap motion indicating a switch request. Eight buffers are presented, and buffer 801 includes all zeros, and thus no pitch tap or switch has been detected. Buffer 802 includes a "1" in the first position, a tertiary exclusion region, and thus the pitch tap or switch detected was not a valid pitch tap or switch. The "1" value progresses sequentially in buffers 803 to 805 within the tertiary exclusion area, and at buffer 806 enters the secondary limitation area, but the primary detection area remains zero, indicating no valid tap. Buffer 807 shows the "1" entering the primary detection region, meeting the criteria or requirement for a valid pitch tap condition being detected resulting in the function associated with the switch/pitch tap occurring or being activated. The pattern for buffer 807 is a pattern that meets the criteria for a valid pitch tap or selection of a switch. In this example, the existence of a valid pitch tap results in an activation of the feature associated with the pitch zone and a reset condition such that all regions in the buffer are set to zero, shown in buffer 808.

Figure 9:
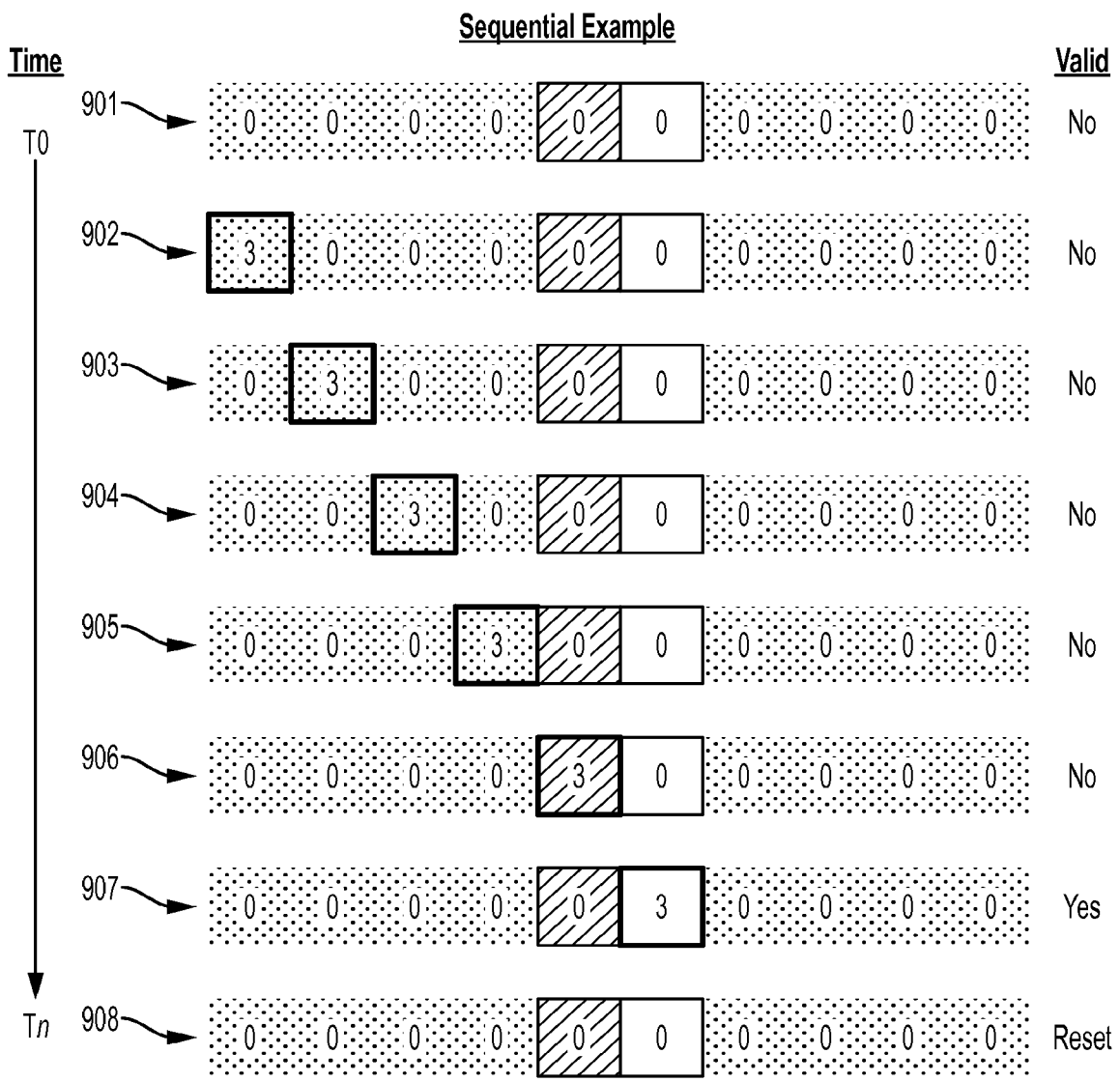
FIG. 9 shows a sequential example of foot pedal tap filtering, such as when the foot pedal treadle enters a desired zone in order to effectuate a switch function.

FIG. 9 illustrates a sequential example for a yaw based tap, but is also applicable to switch clicks or other types of taps. The number "3" indicates an entry into region YP3, indicating a valid yaw tap motion indicating a switch request. Eight buffers are presented, and buffer 901 includes all zeros, and thus no click or switch has been detected. Buffer 902 includes a "3" in the first position, a tertiary exclusion region, and thus the click or switch detected was not a valid click or switch. The "3" value progresses sequentially in buffers 903 to 905 within the tertiary exclusion area, and at buffer 906 enters the secondary limitation area, but the primary detection area remains zero, indicating no valid yaw tap. Buffer 907 shows the "3" entering the primary detection region, meeting the criteria or requirement for a valid yaw tap condition being detected resulting in the function associated with the switch/yaw tap occurring or being activated. The pattern for buffer 907 is a pattern that meets the criteria for a valid yaw tap or selection of a switch. In this example, the existence of a valid yaw tap sensed results in an activation of the feature associated with the yaw zone and a reset condition such that all regions in the buffer are set to zero, shown in buffer 908.

The present design identifies clicks or taps as discrete events over time and prevents false positive readings. Clicks are identified based on proximity of positive readings over time and/or foot pedal treadle angular position for each reading.

Any type of device, such as a twist knob or lever, can be monitored to determine when a switch has been activated in the manner disclosed.

Figure 10:
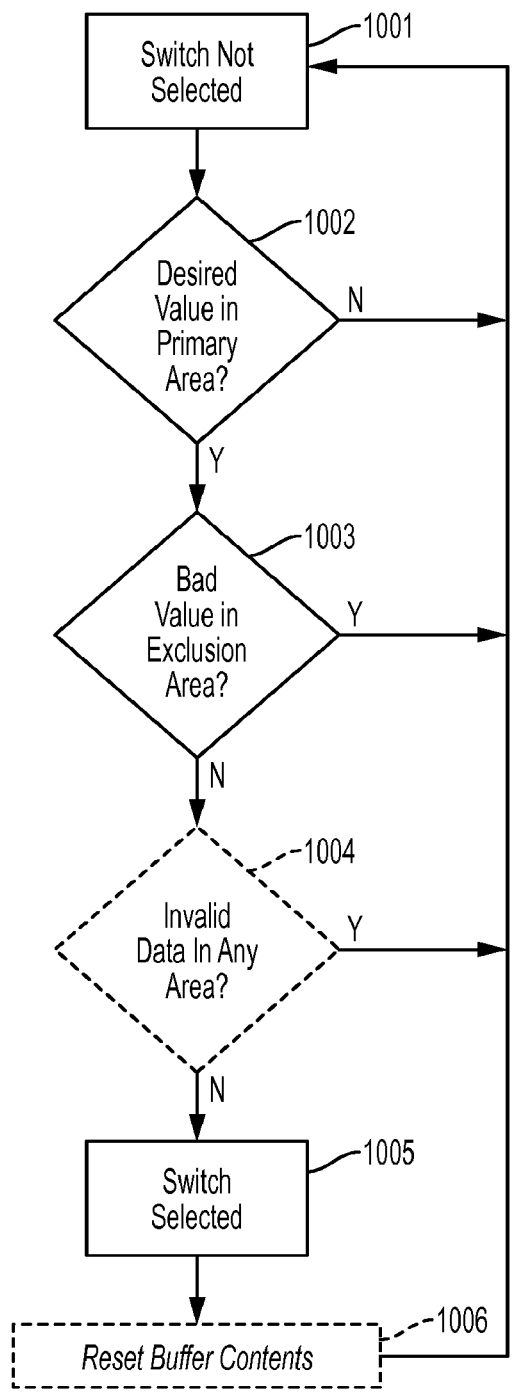
FIG. 10 is a flowchart example of operation of the present design.

An example flowchart representing operation is shown in FIG. 10. From FIG. 10, point 1001 indicates the default state of the switch being unselected—switch undetected. Point 1002 evaluates whether the desired value is in the primary detection region. If not, the system cycles back to point 1001 indicating the switch is undetected. At point 1003, the system determines whether an undesired value is present in an exclusion area, such as the tertiary exclusion area 503 or 504. If so, the system cycles back to position 1001 and the switch is not selected. If not, the system may evaluate whether invalid data is present at point 1004. If invalid data is present, such as invalid data in the secondary limitation area 502 or primary detection area 501, the system transitions to point 1001 and again, no switching has occurred. If, however, no invalid data is present, the desired value is in the primary detection region and no undesired value is in the exclusion area, the system indicates the switch is selected at point 1005, and the buffers may be reset at point 1006. This represents an example, and other conditions may be evaluated as desired, such as evaluating whether a certain amount of time has passed, determining whether conflicting indications are present, and so forth.

Thus the present design includes an ocular surgical apparatus comprising a surgical control device, such as a foot pedal, configured to be employed to control at least one ocular surgical parameter, and a controller configured to receive a series of values from the surgical control device and evaluate the series of values provided from the surgical control device, the series of values provided using a buffer comprising a detection area and an exclusion area. A limitation area may also be provided. Presence of a desired value in the detection area and an absence of a contrary indication in the exclusion area is determined by the controller to indicate a switch associated with the surgical control device is requested by a user of the surgical control device.

Alternately, the present design includes a method for use in an ocular surgical device, comprising operating a surgical control device (e.g. foot pedal) to control at least one ocular surgical parameter, receiving a series of values from the surgical control device using a buffer comprising a detection area and an exclusion area, and controlling a parameter of the ocular surgical device based on contents of the buffer. Presence of a desired value in the detection area and an absence of a contrary indication in the exclusion area indicates a switch associated with the surgical control device is requested by a user of the surgical control device.

One embodiment of the present design includes an ocular surgical apparatus comprising a surgical control device (e.g. foot pedal) configured to be employed to control at least one ocular surgical parameter and a controller configured to receive a series of values from the surgical control device, evaluate the series of values provided from the surgical control device, the series of values provided using a buffer comprising a detection area and an exclusion area, and control an attribute of the ocular surgical apparatus when the series of values indicates a user desires a switch of the attribute based on user input received from the surgical control device. Presence of a desired value in the detection area and an absence of a contrary indication in the exclusion area is determined by the controller to indicate a switch associated with the surgical control device is requested by the user of the surgical control device.

Those of skill in the art will recognize that any step of a method described in connection with an embodiment may be interchanged with another step without departing from the scope of the invention. Those of skill in the art would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present invention.

The various illustrative logical blocks, modules, and circuits described in connection with the embodiments disclosed herein may be implemented or performed using a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in RAM memory, flash memory, ROM memory, DOM memory, EPROM memory, EEPROM memory, registers, hard disk, a removable disk, a CD-ROM, or any other form of storage medium known in the art. An exemplary storage medium is coupled to the processor such the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

The previous description of the disclosed embodiments is provided to enable any person skilled in the art to make or use the present invention. Various modifications to these embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method for use in an ocular surgical apparatus, the method comprising:
   receiving, by a buffer of the ocular surgical apparatus, a series of values from a user-manipulated surgical interface, the buffer comprising a detection area and an exclusion area;
   sequentially evaluating, by a controller of the ocular surgical apparatus, the series of values as provided from the user-manipulated surgical interface;
   controlling at least one ocular surgical parameter of the ocular surgical apparatus based on contents of the buffer;
   wherein a presence of a desired value in the detection area and an absence of a contrary indication in the exclusion area indicate a switch associated with the user-manipulated surgical interface is requested by the user-manipulated surgical interface such that the controller controls the at least one ocular surgical parameter with respect to the switch.

2. The method of claim 1, wherein the user-manipulated surgical interface comprises a foot pedal.

3. The method of claim 1, wherein the buffer further comprises a secondary limitation area and the presence of an unacceptable value in the secondary limitation area indicates no switching is requested by the user-manipulated surgical interface.

4. The method of claim 1, wherein the buffer comprises samples taken at discrete points in time and contents of the buffer progress in a first in, first out (FIFO) manner.

5. The method of claim 1, wherein presence of invalid data in any buffer region indicates no switching is requested by the user-manipulated surgical interface.

6. The method of claim 1, wherein user initiation of a desired movement causes an indication to be provided to the buffer and after a predetermined period of time the indication progresses to the detection area.

7. The method of claim 1, wherein the switch comprises a signal indicating a switch selection.

8. The method of claim 7, wherein the series of values comprise individual and discrete states of the buffer that indicate valid and invalid states for a validation of a receipt of the switch selection.

9. The method of claim 1, wherein the user-manipulated surgical interface enables selection from a plurality of predetermined input options that control the at least one ocular surgical parameter.

* * * * *